United States Patent [19]

Dahms

[11] Patent Number: 4,880,563
[45] Date of Patent: Nov. 14, 1989

[54] COMPOSITION FOR PERSONAL CARE PRODUCT COMPRISING ALKOXYLATED FATTY ALCOHOL AND POLYSILOXANE

[75] Inventor: Gerd Dahms, Velbert, Fed. Rep. of Germany

[73] Assignee: Deutsche ICI GmbH, Frankfurt, Fed. Rep. of Germany

[21] Appl. No.: 890,337

[22] Filed: Jul. 29, 1986

[30] Foreign Application Priority Data

Aug. 1, 1985 [GB] United Kingdom ................ 8519426

[51] Int. Cl.$^4$ ........................ A61K 9/10; B01F 17/42; B01F 17/54
[52] U.S. Cl. .................................. 252/312; 252/309; 514/941; 514/969
[58] Field of Search ................ 252/309, 312; 514/941, 514/969

[56] References Cited

U.S. PATENT DOCUMENTS

| | | | |
|---|---|---|---|
| 3,118,000 | 1/1964 | Dapréet al. | 260/584 |
| 3,968,203 | 7/1976 | Spitzer et al. | 424/47 |
| 4,246,257 | 1/1981 | Elliott et al. | 424/78 |
| 4,265,878 | 5/1981 | Keil | 424/68 |
| 4,268,499 | 5/1981 | Keil | 424/68 |
| 4,268,526 | 5/1981 | Vargas et al. | 424/358 |
| 4,364,837 | 12/1982 | Pader. | |
| 4,435,382 | 3/1984 | Shin et al. | 424/66 |
| 4,511,554 | 4/1985 | Geria et al. . | |
| 4,689,168 | 8/1987 | Requejo | 252/171 |

FOREIGN PATENT DOCUMENTS

| | | |
|---|---|---|
| 0035899 | 9/1981 | European Pat. Off. . |
| 1467676 | 3/1977 | United Kingdom . |
| 2079300 | 1/1982 | United Kingdom . |

OTHER PUBLICATIONS

2176 Seifen-Ole-Fette-Wachse vol. 108 (1982), Sep., No. 14, Augsburg, Deutschland, p. 428-untranslated.
Kirk-Othmer: Encyclopedia of Chemical Technology: vol. 7, p. 151 (1981).

*Primary Examiner*—John F. Terapane
*Assistant Examiner*—Gary Geist
*Attorney, Agent, or Firm*—Cushman, Darby & Cushman

[57] ABSTRACT

A composition for personal care products comprising alkoxylated polyether derived from $C_6$ to $C_{22}$ fatty alcohol in admixture with cyclic dimethyl siloxane pentamer or tetramer, in a weight ratio 5:95 to 95:5 and their use in oil/water or water/oil emulsions, together with processes for their preparation.

5 Claims, No Drawings

COMPOSITION FOR PERSONAL CARE PRODUCT COMPRISING ALKOXYLATED FATTY ALCOHOL AND POLYSILOXANE

This invention relates to a composition for personal care products such as cosmetics comprising alkoxylated fatty alcohol and polysiloxane, useful mainly as a base for the manufacture of creams and lotions. The composition may also be used as, or as a part of, a carrier for physiologically active materials including pharmaceuticals.

The principal purpose of the composition is to enhance the spreadability on the skin of the final product, but it may serve subsidiary purposes as a carrier or emulsifier. Frequently, it will be incorporated into oil/water or water oil emulsions.

Alkoxylated fatty alcohols are a useful component of topical compositions in that they provide an emollient effect. By "emollient" we mean promotion of retention of water. They have certain disadvantages in that they may be of high viscosity and may have a spreadability less than in certain formulations. It is known that spreadability depends upon the surface tension of the material in the air (see R. Keymer : "Zur Spreitung flussiger Lipoide auf der Haut", Pharm. Ind. 32(7), 577-581 (1970). We have found an additive for alkoxylated fatty alcohols which reduces surface tension and hence increase spreadability. Viscosity is also reduced.

The compositions also have advantageous low temperature storage properties.

The additive concerned is a cyclic siloxane in the form of tetramer or pentamer.

PRIOR ART

Cyclic siloxanes are used in topical compositions as a non-aqueous diluent. The cyclic siloxanes of the formula

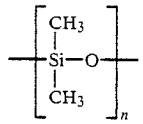

where n is 4 or 5 are also usefully volatile, having boiling points of 175° C. and 210° C. respectively.

It is known from European Patent No. 35899 that such silicones may be included in hair conditioners, in which the active ingredient is a quaternary ammonium compound. Emollients are not mentioned though isopropyl myristate is mentioned as an oil additive. UK patent No. 1 467 676 describes antiperspirants in which volatile silicones replace isopropyl myristate which is described as an emollient. In US patent No. 4 268 499 antiperspirant compositions are described which include cyclic silicone and non-ionic surfactants based on fatty alcohol ethers and polyoxyethylene derivatives. No surfactants containing polyoxypropylene groups are mentioned. US patent 4 246 257 describes a cosmetic cream which may include silicone, waxes, emulsifiers and oils, but no truly emollient material. The compositions of the present invention achieve more than a simple viscosity reduction effect. Oil and water creams and lotions are applied to the skin top to give a moisturing effect. The following authors:

(1) Schrader, K. H. Grundlagen und Rezepturen der Kosmetika, Dr. Huting Verlag, Heidelberg, P. 242, (1979)

(2) Jellinek, J. S.—Moisturizing and Emmolliency Part One, Cosmetic and Toiletries, pp. 69-73 (1978)

(3) Junginger, H.—Aufbau und Entwicklung von Salben, Cremes und Emulsionen : APV Dermatikerkurs II Mainz, 1983, pp. 19-45 show that moisturising, or emolliency, is most effective when so called lamellar liquid crystal phases are present. Formulations containing the composition of the present invention show these phases.

DESCRIPTION OF THE INVENTION

The present invention provides a composition comprising (A) 5-95% by weight of an alkoxylated polyether of the formula

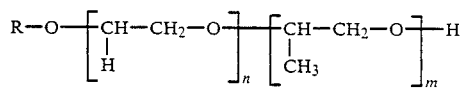

where R is $C_6$–$C_{22}$, saturated or unsaturated and may be substituted;

n is 0 to 10 m is 2 to 50 the different types of alkoxyl group being in random or block relationship; and (B) 95 to 5% by weight of tetra (dimetyl cyclosiloxane) or penta (dimetyl cyclosiloxane) or mixtures thereof.

Preferably the composition comprises components A and B in a weight ratio of 20:80 to 80:20.

The group R is preferably a $C_{10}$–$C_{20}$ hydrocarbyl group, more preferably, for reasons of availability $C_{12}$–$C_{18}$ group. It may be linear or branched, saturated or unsaturated, and may include substituents, such as hydroxyl. In the last mentioned case, the hydroxyl group may be alkoxylated. The value of m is preferably 10-20. The following compounds are examples of those which may be used as component A of the composition of the invention.

POP (4) hydroxystearyl alcohol
POP (15) hydroxystearyl alcohol
POP (4) octyl alcohol
POP (10) cetyl alcohol
POP (4) 12-hydroxystearyl alcohol
POP (6) 12-hydroxystearyl alcohol
POP (15) 12-hydroxystearyl alcohol
POP (5) erucyl alcohol
POP (5) oleyl alcohol Where POP=Polyoxypropylene and the number in brackets represents the number of moles of propylenoxy units included. Polymer units derived from ethylene oxide may be present, but should be kept low in number if it is desired to form a liquid composition.

Compositions according to the invention are made simply by mixing the two components. Further components may be added, perfumes, dyes, waxes and so on, depending upon the application.

Similarly, the composition of the invention may be incorporated into a wide range of personal care and pharmaceutical products, normally for topical application, more particularly skin application.

A useful range of applications for the compositions is to be found in oil in water and water in oil emulsions.

In water in oil emulsions, the composition of the invention, using tetramer siloxane, gives cooling effects on the skin with a lower greasiness sensation. The emollient effect of component B aids water retention and enhances skin elasticity. The admixture of component B reduces the freezing point of tetramer siloxane, thereby adding storage properties. There is no astringent effect associated with the cooling effect, making the compositions suitable for inclusion in sunburn and suntan treatments.

In oil in water lotions and creams use of the composition of the invention enhances the spreadability of the product without leaving the sticky feeling on the skin.

Compositions according to the present invention may be included in a complete cosmetics formulation to the extent of typically of 2 to 30% by weight of the total weight of ingredients, preferably 2 to 10% by weight. An oil/water/emulsifier system will form the main part of the rest of the composition, the emulsifier being typically 3 to 10% by weight of the total. Moisture regulators, thickeners active ingredients, preservatives, perfume oil, colours and pigments may be added in usual amounts.

The invention is illustrated by the following examples. Parts and percentages are given by weight.

EXAMPLE 1

POP (15) stearyl alcohol (A) and tetra (dimethyl cyclosiloxane) (B) were mixed together in various proportions and the melting point of the mixture was determined. For certain compositions, surface tension was measured. Pure components and their properties are included in the table below for comparative purposes.

| Composition | | | Property | |
|---|---|---|---|---|
| Parts of | | | Melting point | Surface tension |
| N | A | B | (C.) | (mN/m) |
| 1 | 100 | 0 | 2 | 33.0 |
| 2 | 90 | 10 | 1 | — |
| 3 | 80 | 20 | −1 | 26.0 |
| 4 | 70 | 30 | 1 | — |
| 5 | 66 | 33 | — | — |
| 6 | 60 | 40 | 6 | — |
| 7 | 50 | 50 | 6 | 21.4 |
| 8 | 40 | 60 | 9 | — |
| 9 | 33 | 66 | — | — |
| 10 | 30 | 70 | 9 | — |
| 11 | 20 | 80 | 7 | 20.0 |
| 12 | 10 | 90 | 10 | — |
| 13 | 0 | 100 | 17 | 19.3 |

It will be seen that the disadvantageously high melting point and surface tension of the siloxane is reduced by quite small amounts of added stearyl alcohol ether, and further additions give less marked changes.

EXAMPLE 2

A water in oil lotion was prepared as follows, using a composition from example 1.

| | | % weight |
|---|---|---|
| Oil phase: | Composition No 11 | 10.0 |
| | Paraffin oil | 6.0 |
| | Petrolatum | 2.0 |
| | Emulsifier POE (7) | 6.0 |
| | Hydrogenated castor wax | |
| Water phase: | POE (30) Sorbitol | 4.0 |
| | Preservative | q.s. |
| | Water | to 100 |

Procedure:

1. Heat the oil phase to 40–60 deg. C. and mix;
2. Heat the water phase to 4–060 deg. C., mix and add slowly to the oil; phase using a high shear mixer.
3. Continue mixing for 30 minutes whilst cooling to room temperature.

Assessment:

The product lotion is moisterising, water resistant and gives a tack-free skin feel. It has a refreshing cooling effect on application with a dry lubrication after feel. As active ingredients, sunscreen agents, allantoin, collagen and vitamins could be incorporated without loss of emulsion properties.

EXAMPLE 3

A water in oil cream was prepared as follows

| | | % weight |
|---|---|---|
| Oil phase: | Composition No 8 | 6.0 |
| | Paraffin oil | 5.0 |
| | Petrolatum | 3.0 |
| | Emulsifier POE (1) | 10.0 |
| | Glycerol sorbitan Oleostearate | |
| Water phase: | POE (30) Sorbitol | 4.0 |
| | Preservative | q.s. |
| | Water | to 100 |

Procedure:

1. Preheat oil phase to 70–80 deg. C. and mix
2. Heat water phase to 70–80 deg. C. and add slowly to the oil phase using a MIG mixer
3. Continue mixing for 30 minutes whilst cooling to room temperature.

Assessment:

The cream was moisturising, water resistant and tack-free after use, giving a dry lubricating effect. Active ingredients described in Example 1 could also be incorporated.

EXAMPLE 4

An oil in water lotion was prepared as follows

| | | % weight |
|---|---|---|
| Oil phase: | Composition No 7 | 4.0 |
| | Isopropylmyristate | 2.0 |
| | Paraffin oil | 5.0 |
| | Petrolatum | 3.0 |
| | Emulsifier: POE (5) Stearylstearate | 4.0 |
| | Emulsifier: POE (12) Stearylalcohol | 2.0 |
| Water phase: | POE (30) sorbitol | 4.0 |
| | Preservative | q.s. |
| | Water | to 100 |

Procedure:

1. Heat oil phase to 50°–60° C. and mix;
2. Heat oil phase to 60°–70° C. and add preheated oil phase whilst homogenising using a high speed, high shear mixer e.g. Silverson type;
3. After forming the emulsion continue mixing at reduced speed with cooling to room temperature.

Assessment:

The soft oil-in-water lotion produced showed lamella liquid crystal phases, with water retaining ability and a good moisturing effect.

EXAMPLE 5

An oil in water cream prepared as follows

| Component | | % weight |
|---|---|---|
| Oil phase: | Component No 5 | 4.0 |
| | Isopropylmyristate | 2.0 |
| | Paraffin oil | 5.0 |
| | Stearic acid | 2.0 |
| | Glycerol monostearate | 3.5 |
| | Emulsifier: POE (21) Stearylalcohol | 3.0 |
| | Emulsifier: POE (2) Stearylalcohol | 1.0 |
| Water phase: | POE (30) sorbitol | 4.0 |
| | Preservative | q.s. |
| | Water | to 100 |

Procedure:
1. Heat oil phase to 50°-60° C. and mix;
2. Heat water phase to 60°-70° C. and the add preheated oil phase whilst homogenising using a high speed, high shear mixer e.g. Silverson type;
3. After forming the emulsion continue mixing at reduced speed with cooling to room temperature.

Assessment:
The product is a non-greasy, quick penetrating moisturising skin cream. Lamellar liquid crystal phases are present.

What I claim is:

1. An emollient composition consisting of:
   (A) 5-95% by weight of an alkoxylated polyether of the formula:

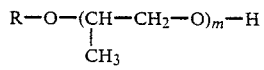

swhere
   R is a $C_6$ to $C_{22}$ hydrocarbyl group, saturated or unsaturated and may be substituted; and
   m is 2 to 50; and
   (B) 95-5% by weight of tetra(dimethylcyclosiloxane) or penta(dimentylcyclosiloxane) or mixtures thereof.

2. Oil in water or water in oil emulsion containing from 2 to 30% by weight of an emollient composition which is included in the oil phase and consists essentially of
   (A) 5-95% by weight, relative to the weight of the emollient composition, of an alkoxylated polyether of the formula:

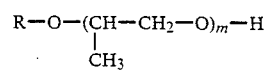

where
   R is a $C_6$ to $C_{22}$ hydrocarbyl group, saturated or unsaturated and may be substituted; and
   m is 2 to 50; and
   (B) 95-5% by weight, relative to the weight of the emollient composition, of tetra(dimethylcyclosiloxane) or penta(dimethylcyclosiloxane) or mixtures thereof.

3. A composition according to claim 2 in which the weight ratio of A to B is from 20:80 to 80:20.

4. A composition according to claim 2 in which R is $C_{12}$ to $C_{18}$ and m is 10 to 20.

5. The emulsion of claim 2 which is a water in oil emulsion.

* * * * *